United States Patent [19]

Gochanour

[11] Patent Number: 5,774,889
[45] Date of Patent: Jul. 7, 1998

[54] PROTECTIVE HAND COVERING

[76] Inventor: G. Gary Gochanour, 3108 Baker Rd., Dexter, Mich. 48130

[21] Appl. No.: 725,831

[22] Filed: Oct. 7, 1996

[51] Int. Cl.⁶ .................................................. A41D 13/08
[52] U.S. Cl. .................... 2/16; 2/161.6; 2/161.7; 2/158
[58] Field of Search .................. 2/16, 21, 60, 159, 2/158, 161.6, 161.7, 161.8, 167, 168; 428/40.1, 41.7, 41.8, 42.3, 343, 349; 602/54, 62

[56] References Cited

U.S. PATENT DOCUMENTS

| | | |
|---|---|---|
| 356,385 | 1/1887 | Waterhouse . |
| 1,486,006 | 12/1924 | Blom . |
| 1,731,340 | 10/1929 | Lambert .................................. 2/158 |
| 2,751,592 | 6/1956 | Longstreth et al. ....................... 2/21 |
| 2,773,264 | 6/1956 | Nover . |
| 2,864,090 | 12/1958 | Sutherland ............................. 2/161.7 |
| 3,260,260 | 7/1966 | Questel . |
| 3,387,307 | 6/1968 | Blatz . |
| 3,645,835 | 2/1972 | Hodgson . |
| 4,017,907 | 4/1977 | Margolis ................................. 2/158 |
| 4,034,853 | 7/1977 | Smith .................................... 2/169 |
| 4,804,432 | 2/1989 | Jurrins et al. . |
| 4,832,650 | 5/1989 | Tong . |
| 4,884,300 | 12/1989 | Vistins ................................... 2/162 |
| 4,913,897 | 4/1990 | Chvapil et al. . |
| 4,916,757 | 4/1990 | Berlin et al. ............................. 2/159 |
| 4,938,515 | 7/1990 | Fazio .................................... 2/21 |
| 5,012,801 | 5/1991 | Feret . |
| 5,018,516 | 5/1991 | Gilman . |
| 5,020,160 | 6/1991 | Cano .................................... 2/159 |
| 5,024,217 | 6/1991 | Spencer . |
| 5,172,424 | 12/1992 | Adkins .................................. 2/21 |
| 5,210,880 | 5/1993 | Yale ..................................... 2/159 |
| 5,566,390 | 10/1996 | Clancy .................................. 2/16 |
| 5,575,014 | 11/1996 | Kane et al. .............................. 2/16 |
| 5,636,406 | 6/1997 | Strong .................................. 15/227 |

FOREIGN PATENT DOCUMENTS

| | | | |
|---|---|---|---|
| 2542980 | 9/1984 | France ................................... 2/158 |
| 4135973 | 5/1993 | Germany ............................... 2/16 |
| WO 89/00385 | 9/1989 | WIPO .................................. 2/16 |

*Primary Examiner*—Amy B. Vanatta
*Attorney, Agent, or Firm*—Gifford, Krass, Groh, Sprinkle, Patmore, Anderson&Citkowski

[57] ABSTRACT

A protective hand covering for adhering to the user's hand. Pressure-sensitive adhesive is applied to the back surface of a sheet of thin flexible film, which is shaped to cover a protected area of the user's hand. The pressure-sensitive adhesive provides a sufficiently strong bond to prevent the hand covering from being inadvertently dislodged, but a sufficiently weak bond to allow the hand covering to be removed without injuring the user. The film is sufficiently impervious to contaminates to prevent the transfer of contaminates from the substance or object being handled to the user and vice versa.

8 Claims, 2 Drawing Sheets

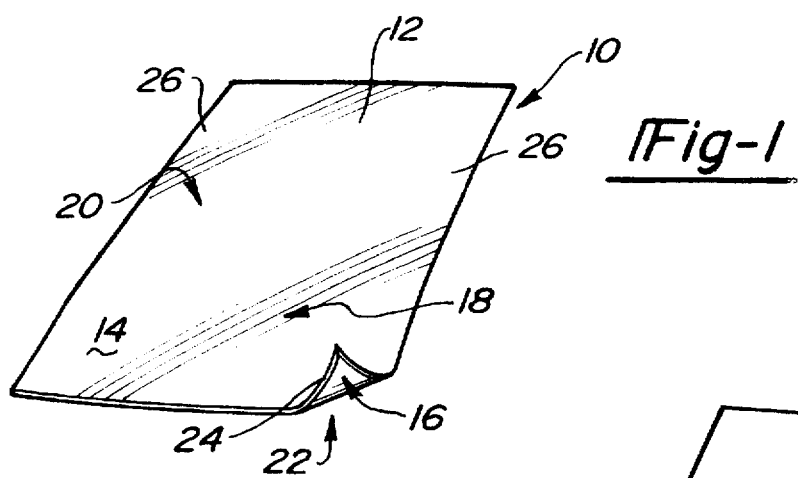
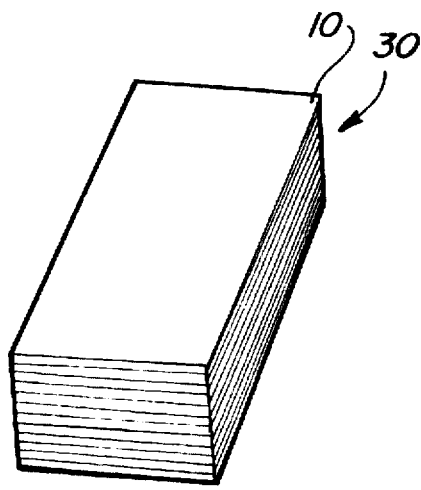
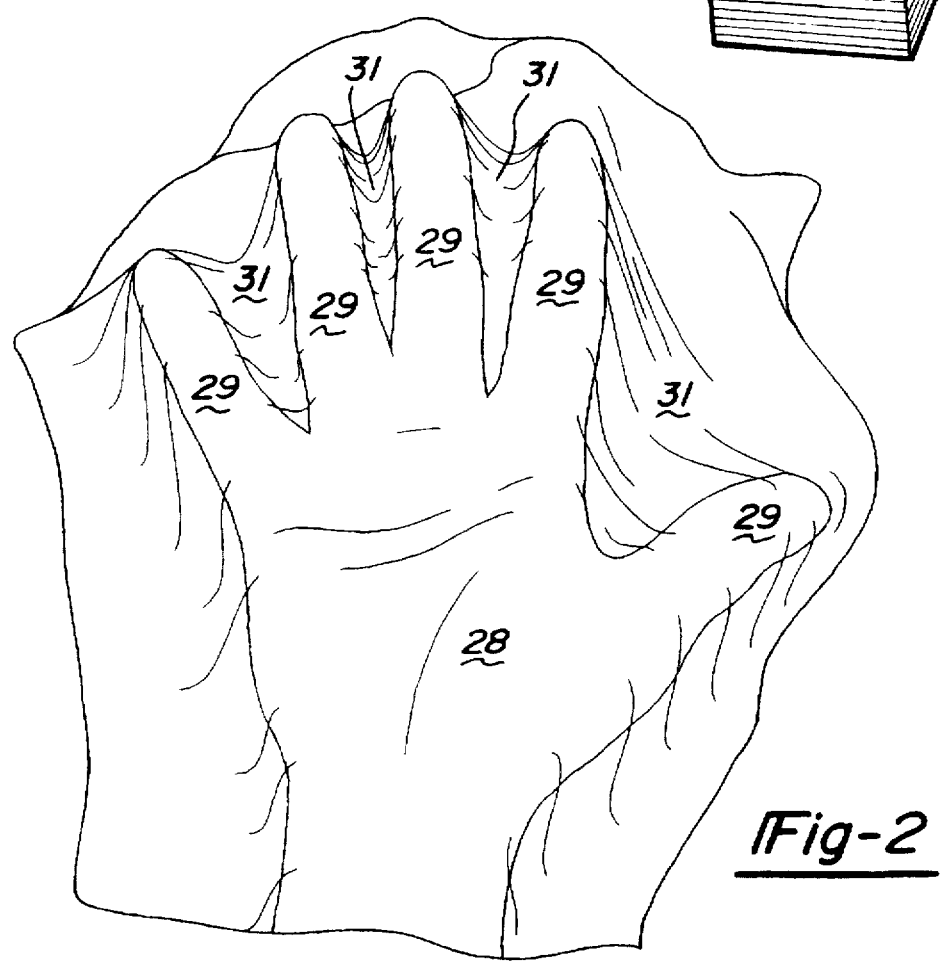

PROTECTIVE HAND COVERING

BACKGROUND AND SUMMARY OF THE INVENTION

This invention is related to protective hand coverings and particularly to a protective hand covering formed from a sheet of thin flexible film backed by a pressure-sensitive adhesive. The adhesive allows the hand covering to be temporarily bonded to the user's hand during use.

In many fields, such as the dental, medical, food service, laboratory, and precision manufacturing fields, reducing the potential for contamination is a primary concern. Because workers in these fields routinely manually handle contaminated or contaminatable materials, it is critical that some type of barrier be interposed between the hands of the workers and the contaminated or contaminatable materials. Typically, this barrier comprises a latex or plastic film glove or mitten. The user places their hand into the glove or mitten prior to handling the contaminated or contaminatable materials and this prevents contamination from being transferred to or from the substance or object being handled.

There are primarily three routes for the transfer of contaminates. The first route is the transfer of contaminates from the contaminated material to the user handling the contaminated material. In the dental, medical and other health care fields, the AIDS epidemic has heightened awareness of the possibility of patients infecting their health care workers with the HIV virus through exposure to body fluids. Even before AIDS was a concern, however, the presence of other highly contagious infectious agents, such as hepatitis, justifiably caused serious concerns among health care workers and resulted in procedures and precautions being implemented for reducing this possible route of contamination. For industrial and laboratory workers handling toxic or hazardous materials, particularly persistent toxins such as mercury, lead and pesticides, extreme precautions are taken to avoid any worker exposure to these materials.

A second route is the transfer of contaminates from the user to the contaminatable object or materials being handled. Some types of computer and electrical components, such as disk drive storage media and halogen light bulbs, can be ruined by being merely touched with an unprotected hand. Detectable amounts of oil, moisture, skin flakes, etc. will inevitably be transferred to any object which is handled with an unprotected hand. Laboratory samples and crime scene evidence are two other types of materials that can easily be contaminated if proper protective hand coverings are not worn.

A third route for contamination is the transfer of contaminates from an earlier object handled by a worker to a later object handled by that worker or a co-worker. This third route is often the most difficult to control because the contamination may be indirect (i.e. it may not be directly from the earlier object to the worker to the later object).

Health care workers typically remove their old gloves and put on new gloves prior to examining or treating a new patient. What may be overlooked, however, is that when their gloves become contaminated during examination or treatment of a patient, any object touched by these gloves, such as a door handle, a pen, a drawer handle, or treatment equipment, may itself become contaminated. When handling particularly virulent infectious agents, an attempt may made to use cleaning or sterilizing agents, such as chemical solutions, to remove or neutralize contaminates which have been transferred to these areas. Remedial measures, such as applying cleaning or sterilizing agents, are typically less than completely effective in eliminating contamination. Similar issues arise when industrial or laboratory workers handle toxic, hazardous or contaminated materials. The preferred method for eliminating this route for contamination is to eliminate the contamination of these areas altogether.

A primary reason these areas become contaminated is the difficulty of removing and putting on typical hand coverings. Typical hand coverings require that the hand or a portion of the hand be place inside and positioned with respect to a closed section of the hand covering. It can take a greater part of a minute to remove a contaminated pair of conventional latex gloves, replace them with a new pair and properly position the new gloves over the user's hands. If after handling potentially contaminated materials, a health care worker must operate treatment equipment, the worker must first remove their current pair of gloves and then put on a new pair of gloves before handling the equipment. To avoid accidentally contaminating the patient with contaminates that may have been present on the machine, the worker must then remove this second pair of gloves and put on a third pair of gloves before again coming into contact with the patient.

In view of the above and other limitations of the prior art, a primary object of the present invention is to provide a type of protective hand covering which may be easily and quickly put on and removed by the user. Instead of requiring the user to place their hand into a closed section of the hand covering and then position their hand with respect to the hand covering to obtain a proper fit, the inventive protective hand covering is put on simply by bringing an open hand into contact with the pressure-sensitive adhesive on the back surface of the thin flexible film. If the hand is properly positioned with respect to the inventive protective hand covering as it is brought into contact with the pressure-sensitive adhesive, no repositioning of their hand with respect to the hand covering is required to obtain a proper fit. By substantially decreasing the time it takes to remove and put on hand coverings, the time required to perform certain types of procedures can be dramatically reduced. Increasing the ease of putting on and removing hand coverings will also encourage workers to put on new hand coverings more frequently, which will in turn reduce the likelihood of indirect contamination. Because the inventive protective hand covering may be put on in only a second or two, new hand coverings can be put on for each patient even when every second is crucial.

A further object is to provide a protective hand covering which may be placed directly over other hand coverings, including conventional latex gloves or the present inventive protective hand coverings, already on the hand of the user. This will allow a user already wearing a contaminated hand covering to put on the inventive hand covering and handle an object without contaminating it and without taking the time required to remove the existing contaminated hand covering. As such, the present invention is beneficial where a health care worker must operate treatment equipment after their existing hand covering has been contaminated. To avoid contaminating the equipment, the worker can place the inventive hand covering over their existing hand covering and operate the treatment equipment without concern.

The inventive hand covering may also reduce the total number of hand coverings needed for certain procedures. If the worker described above again needs to come into contact with the patient, the now contaminated inventive hand covering may simply be removed. Because the inventive hand covering prevented the existing hand covering from being contaminated by contact with the equipment, the existing hand covering would generally not be removed and replaced before the worker again comes into contact with the patient.

The inventive hand covering is also fabricated from substantially less material than a conventional hand covering and this results in less waste being generated when the hand covering is disposed of. This reduction waste quantity will result in cost savings compared to the cost of disposing conventional hand coverings.

The inventive hand coverings are also anticipated to be more cost effective to manufacture than conventional gloves or mittens.

Further objects, features and advantages of the invention will become apparent from a consideration of the following description and the appended claims when taken in connection with the accompanying drawings.

BRIEF DESCRIPTION OF THE DRAWINGS

FIG. 1 is a top down view of the back surface of a protective hand covering in accordance with this invention with a corner turned up to show a portion of the front surface;

FIG. 2 is a perspective view of the protective hand covering from FIG. 1 after it has been adhered to the hand of a user;

FIG. 3 is a tablet formed by a plurality of protective hand coverings located on top of one another;

DETAILED DESCRIPTION OF THE PREFERRED EMBODIMENT

Figure 4A:
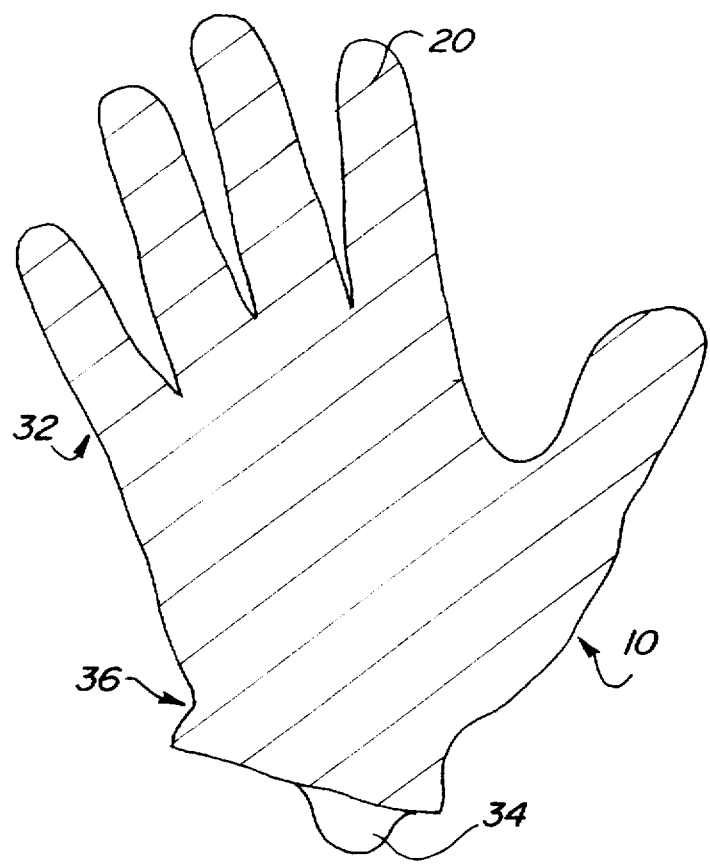
FIGS. 4A and 4B are alternative shapes and patterns of adhesive application for the inventive protective hand covering.

A rectangular whole-hand version of the protective hand covering in accordance with this invention is shown in FIG. 1 and is generally designated by reference number 10. The protective hand covering 10 comprises a sheet 12 of thin flexible film 14 which has a front surface 16 and a back surface 18. A pressure-sensitive adhesive 20 is distributed on the back surface 18 of the thin flexible film 14. A corner 22 of protective hand covering 10 is turned up in FIG. 1 to allow the side surface 24 and front surface 16 of the hand covering to be viewed.

The sheet 12 of thin flexible film 14 is preferably slightly oversized with respect to the portion of the users hand intended to be covered by the protective hand covering. The oversized edge portions 26 of the sheet 12 are designed to wrap around and adhere to the sides and a portion of the back of the user's hand for reasons further discussed below. In FIG. 1, pressure-sensitive adhesive 20 has been uniformly applied to the entire back surface 18 of thin flexible film 14.

In FIG. 2, the protective hand covering 10 from FIG. 1 is shown as it is used, adhered to the palm of a user's hand 28 resulting in film webs 31. As can be seen in FIG. 2, the oversized edge portions 26 of inventive protective hand covering 10 are adhered to the sides and a portion of the back surface of the user's hand 28. The process of adhering the oversized edge portions 26 to the sides and a portion of the back surface of the user's hand 28 is as simple as pressing the palms of the hands together after a protective hand covering has been adhered to each hand and then interleaving fingers 29 to stretch the film webs 31. Oversized edge portions 26 prevent contaminates being transferred to or from the portion of the users hand 28 covered by this portion of the protective hand covering 10. Oversized edge portions 26 also help to prevent protective hand covering 10 from being inadvertently dislodged during use and also helps to prevent substances or objects from sliding between the protective hand covering and the user's hand from the edges of the protective hand covering as it is being used.

Thin flexible film 14 must substantially inhibit the transfer of contaminates from the protected area of the user's hand to the potentially contaminated or contaminatable substance or object as well as the transfer of contaminates from the potentially contaminated or contaminatable substance or object to the protected area of the user's hand. In many cases, a material that is impervious to liquids, such as a plastic, polymer, rubber or latex film or a coated paper sheet, will sufficiently inhibit the transfer of the contaminates at issue. In other cases, the contaminates, such as organic solvents, or the operating environment, such as extremely high or low temperatures, require a film that has enhanced barrier or performance characteristics. In certain applications, a film which allows some substances to pass through the film, such as water vapor, while acting as a barrier to other substances, such as bacteria, is preferred. This film can also be a laminate of dissimilar materials to obtain the proper barrier and performance characteristics.

Thin flexible film 14 must be strong enough to avoid being cut, torn or punctured during use. If an opening is formed in the film as the protective hand covering is used, contaminates can transfer freely from the substance or object being handled to the user's hand and vice versa. The strength requirements of the film will primarily depend on the types of materials being handled, the type of handling these materials typically required, and the expected duration of use of the protective hand covering.

Thin flexible film 14 should be sufficiently soft and pliable to allow the user to maintain significant dexterity after the protective hand covering 10 has been adhered to their hand and to allow the user to freely and independently manipulate their fingers through the hand covering. Thin flexible film 14 will preferably be transparent to allow the protected area of the user's hand to be visible after the protective hand covering has been adhered. It is also desirable to manufacture thin flexible film 14 from a biodegradable material.

Antibacterial agents or other contaminate neutralizing or absorbing materials can be incorporated into the thin flexible film 14 or applied to the front or back surface of the thin flexible film. The front surface 16 of the thin flexible film 14 could also be texturized to reduce the likelihood that an object being handled by a user of the protective hand covering will slip from the user's hand.

A 1.0 mil thick polyurethane film used as a carrier for a product marketed by Avery Dennison, Specialty Tape Division, 250 Chester Street, Painesville, Ohio 44077 as MED 5020 has generally acceptable performance properties as a thin flexible film 14 for many dental and medical purposes for the inventive protective hand covering 10. This film has a typical tensile strength between 5,000 and 8,000 psi and an elongation between 400 and 700%. This film acts as a bacterial barrier, yet has a high moisture vapor transmission rate which would allow moisture from the user's hand to be released as the protective hand covering is being used, rather than trapped by the film. This film is very soft and pliable, which allows the user to maintain significant dexterity after the hand covering has been put on and allows the user to freely and independently manipulate their fingers. This film is transparent, which allows the protected portion of the user's hand to be visible after protective hand covering 10 has been put on. For many applications, linear low density polyethylene or polyurethane films are generally suitable materials for thin flexible film 14.

The pressure-sensitive adhesive 20 must be capable of providing a sufficiently strong bond when adhered to the user's hand to inhibit the inventive protective hand covering from being dislodged during use. The adhesive must also offer a sufficiently weak bond to allow the hand covering to be removed without damaging the user's hand. Because the protective hand covering 10 may be applied over other hand coverings, such as a conventional latex glove or the present inventive protective hand covering 10, the adhesive characteristics of the pressure-sensitive adhesive with respect to the external surface of these types of hand coverings must also be considered.

Pressure-sensitive adhesive 20 will preferably be comprised of medical and food contact grade substances which will be nonirritating and nonsensitizing in humans.

Pressure-sensitive adhesive 20 could consist of a waxy material, such as microwax SP18 from Strahl and Pitch, an acrylic adhesive such as ARcare 7396 or ARcare 8072 from Adhesives Research, Inc., Glen Rock, Pa., a hot melt adhesive, such as HL2306-x, HM1902 or HL2385-x from H. B. Fuller Company, Vadnais Heights, Minn., or a conventional pressure-sensitive adhesive, such as Duro-Tac 4227 from National Starch and Chemical, Bridgewater, N. J.

Pressure-sensitive adhesive 20 could also be a tacking resin such as ESCOREZ or Vistanex polyisobutylene LM from Exxon. This tacking resin could be placed on the back surface 18 of thin flexible film 14 or could be mixed into the material forming thin flexible film 14.

Pressure-sensitive adhesive 20 will generally be applied to the back surface 18 of thin flexible film 14 around at least the periphery of the sheet 12, where the thin flexible film 14 will contact the portion of the user's hand 28 being protected by the inventive protective hand covering 10.

Sufficient pressure-sensitive adhesive 20 should be applied to the back surface 18 of thin flexible film 14 to assure that protective hand covering 10 is not dislodged during use. Pressure-sensitive adhesive 20 should be applied to the back surface 18 of the thin flexible film 14 wherever it is critical that the film be adjacent to the user's hand.

It is also possible to adhere protective hand covering 10 to the user's hand 28 through the use of electrostatic attraction. A positive or negative electrical charge can be introduced into the protective hand covering 10 and an opposite electrical charge can be introduced into the user's hand 28. These opposing electrical charges will cause the protective hand covering 10 to be attracted to and adhered to the user's hand 28. To obtain a sufficient electrical charge to firmly adhere protective hand covering 10 to the user's hand 28, an electrically conductive material may be incorporated within or attached to thin flexible film 14. To obtain an appropriate opposite electrical charge, the user of protective hand covering 10 may step on a floor mat, touch a charged electrical conductor, or be physically connected to an electrical source before their hand is brought into contact with protective hand covering 10.

As an alternative, the thin flexible film 14 and adhesive 20 could be provided as a single component. For example, the user's hand could be dipped in a liquid silicone or latex bath, thereby coating the user's hand with a suitable thin flexible film 14. The latex or silicone could be provided in a composition that readily cures upon exposure to air or ultraviolet light. When the protective hand covering 10 is no longer required, the thin flexible film 14 can be removed from the user's hand by merely peeling the sheet away.

Several methods for packaging and dispensing the inventive protective hand coverings are feasible. FIG. 3 shows a stack of protective hand coverings 10 which are packaged in tablet format. Tablet 30 is formed by joining a plurality of protective hand coverings 10, either a common edge or the back surface of each protective hand covering being joined to front surface of the protective hand covering directly above it. The affinity of the adhesive for the opposing surface of the adjacent sheet would need to be, in this instance, less than the affinity of the adhesive for the user's hand. This could be accomplished by treating front surface 16 with a release coating such as silicone or petroleum gel. In this way, individual sheets can be removed from the tablet allowing the user to merely place one hand on the tablet and then lift his hand from the tablet to remove a sheet, repeating the same for the other hand. In other packaging and dispensing methods, each hand covering or pair of hand coverings are attached to a liner sheet. These hand covering/liner sheets can also be packaged in tablet format. Instead of a tablet format, the sheets could also be joined in fan-fold format (i.e. the first and second sheets are bound at the back, the second and third sheets are bound at the front, the third and fourth sheets are bound at the back, etc.). The hand coverings could also be dispensed from a continuous roll or attached to a continuous roll of liner sheet which could be mounted in a holder. A grab knob linked to a ratchet mechanism could be used to advance the liner sheet the appropriate amount which would make the protective hand coverings available to the user.

Figure 4B:
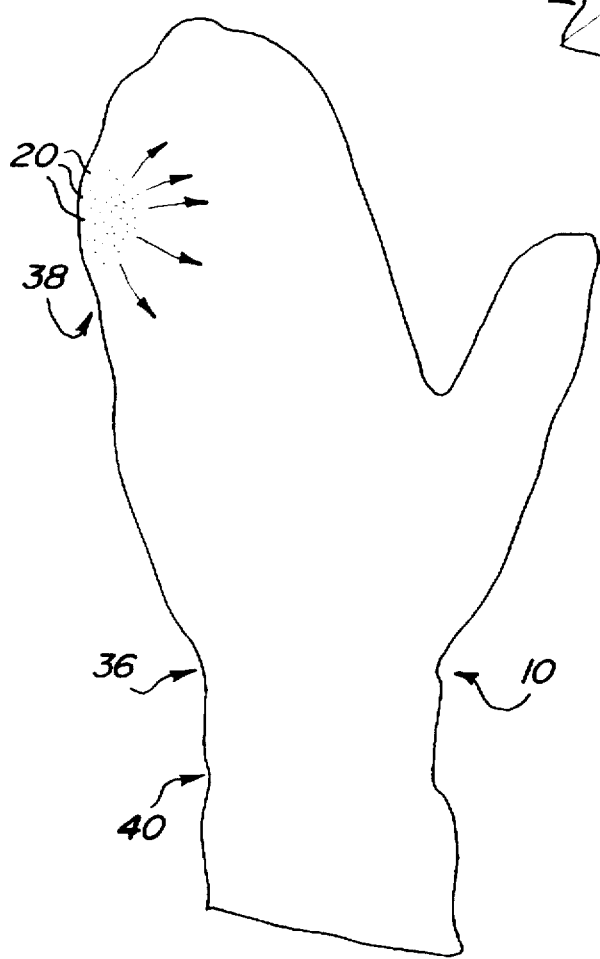

FIGS. 4A, and 4B represent two of a wide variety of alternative shapes which are possible for the inventive protective hand covering 10. FIGS. 4A and 4B also show two alternative patterns for applying pressure-sensitive adhesive 20 to the back surface 18 of the sheet of thin flexible film 14. FIG. 4A shows a five-finger whole-hand design 32 for the hand covering with the pressure-sensitive adhesive 20 being applied as a series of parallel stripes across the back surface of the film. A removal tab 34 portion, which does not have pressure-sensitive adhesive 20 applied to it, is shown in FIG. 4A at the bottom of the wrist portion 36 of the hand covering. The removal tab 34 will facilitate the removal of the protective hand covering 10 after it has been adhered to the user's hand by providing a tab or flap of the thin flexible film material that is not adhered to the hand of the user that can be grasped by the user as they begin to peel off the protective hand covering. FIG. 4B shows a mitten design 38 for the hand covering with the pressure-sensitive adhesive 20 being applied as a plurality of discontinuous dots on the back surface of the film. An upper forearm portion 40 has been added at the bottom of the wrist portion 36 of the mitten design 38 to prevent contamination to or from the upper forearm of the user. Protective hand covering 10 could also be formed in a kidney bean shaped design which covers the fingers and thumb of a user's hand and the upper portion of the palm. Because objects being handled are frequently touched only by these portions of the user's hand, covering only these areas of the user's hand will be sufficient for many purposes. Other possible designs include a paddle design or a three-finger partial-hand design.

As seen by the examples in FIGS. 1, 4A, and 4B, the adhesive may be distributed on the back surface in a wide variety of uniform patterns, such as a solid film, narrow stripes, broad stripes, dots, grid, etc. or nonuniform patterns, such as only at the periphery of the thin flexible film, in strategic locations, etc.

It is to be understood that the invention is not limited to the exact construction illustrated and described above, but that various changes and modifications may be made without departing from the spirit and scope of the invention as defined in the following claims.

I claim:

1. A protective hand covering for adhering to a user's hand before the user touches a contaminated or contaminatable substance, the user's hand having a palmar surface, a back surface, sides and fingers, said protective hand covering comprising:

a sheet of thin flexible film having a front surface and a rear surface, said sheet being sized to cover the palmar surface of the hand with the fingers outstretched, thereby forming film webs between the outstretched fingers, said film being sufficiently stretchable that when the fingers of the hand being covered area interleaved with the fingers of the user's other hand said film web stretch to cover the sides and a portion of the back surface of the user's hand while maintaining the individual manipulation of the use's fingers, said film being sufficiently impervious to contaminates to substantially inhibit the transfer of contaminates from the user's hand to the contaminated or contaminatable substance and the transfer of contaminates from the contaminated or contaminatable substance to the user's hand, pressure-sensitive adhesive distributed about said rear surface, said pressure-sensitive adhesive providing a sufficiently strong bond when adhered to the user's hand to inhibit said sheet from being inadvertently dislodged therefrom, and said pressure-sensitive adhesive providing a sufficiently weak bond when adhered to the user's hand to allow said pressure-sensitive adhesive and said sheet to be removed without injuring the user's hand, by peeling said sheet away from the user's hand.

2. A protective hand covering according to claim 1 wherein said pressure-sensitive adhesive is applied over the entire said rear surface of said sheet.

3. A protective hand covering according to claim 1 wherein said sheet defines an aseptic barrier to infectious agents.

4. A protective hand covering according to claim 1 wherein said sheet is linear low density polyethylene film.

5. A protective hand covering according to claim 1 wherein said sheet is stretchable with an elongation of at least approximately 400%.

6. A protective hand covering according to claim 1 wherein said sheet is generally rectangular in shape.

7. A protective hand covering for adhering to a user's hand before the user touches a contaminated or contaminatable substance, the user's hand having a palmar surface, a back surface, sides and fingers, said protective hand covering comprising:

a sheet of thin flexible film, having a front surface, a rear surface and being of a generally rectangular shape with a size to cover the palmar surface, the sides and a portion of the back surface of the user's hand, said sheet comprising pliable linear low density polyethylene film, pressure-sensitive adhesive distributed about said rear surface of said sheet, said pressure-sensitive adhesive providing a sufficiently strong bond when adhered to the users hand to inhibit said sheet from being inadvertently dislodged therefrom, said pressure-sensitive adhesive providing a sufficiently weak bond when adhered to the user's hand to allow said pressure-sensitive adhesive and said sheet to be removed, without injuring the users hand, by peeling said sheet away from the user's hand, said sheet being sized to receive the palmar surface of the user's hand while the fingers of the user's hand are fanned apart, said sheet including portions defining a webbing between the fingers of the user's hand and having oversized edge portions such that said sheet covers the sides and a portion of the back surface of the users hand after pressing the palms of the user's hands together and interleaving the fingers to stretch said webbing, and said film being sufficiently soft and pliable to permit the user's fingers to be freely and independently manipulable with said webbing stretched therebetween.

8. A method of covering a person's hand, comprising the steps of:

providing a sheet of thin, flexible film having a front surface and a rear surface, the rear surface of the film including a layer of pressure-sensitive adhesive, the area defined by the film being large enough to cover portions of the sides and back of the hand when the hand is outstretched and flattened with the film adhered thereto;

adhering the rear surface of the film to the palmar surface of the hand so as to create webs between the fingers of the hand; and interleaving the fingers of the hand being covered with the fingers of the person's other hand, thereby causing the webs to stretch and cover the sides and a back portion of the user's hand while retaining the user's manual dexterity.

* * * * *

UNITED STATES PATENT AND TRADEMARK OFFICE
CERTIFICATE OF CORRECTION

PATENT NO. : 5,774,889
DATED : July 7, 1998
INVENTOR(S) : Gochanour

It is certified that error appears in the above-identified patent and that said Letters Patent is hereby corrected as shown below:

Column 3, line 22: Replace "comer" with --corner--.

Column 3, line 42: Replace "comer" with --corner--.

Column 3, line 47: Replace "users" with --user's--.

Column 3, line 66: Replace "users" with --user's--.

Column 7, line 16: Replace "area" with --are--.

Column 7, line 17: Replace "web" with --webs--.

Column 7, line 20: Replace "use's" with --user's--.

Signed and Sealed this

Twenty-fourth Day of November, 1998

Attest:

BRUCE LEHMAN

Attesting Officer

Commissioner of Patents and Trademarks